(12) United States Patent
Gung et al.

(10) Patent No.: US 9,296,738 B2
(45) Date of Patent: Mar. 29, 2016

(54) ORGANIC ELECTROLUMINESCENT MATERIAL, THE PROCESS FOR PREPARING THE SAME AND OLED DEVICE USING THE SAME

(71) Applicant: EverDisplay Optronics (Shanghai) Limited, Shanghai (CN)

(72) Inventors: Chihhao Gung, Shanghai (CN); Hongling Yang, Shanghai (CN)

(73) Assignee: EverDisplay Optronics (Shanghai) Limited, Shanghai (CN)

( * ) Notice: Subject to any disclaimer, the term of this patent is extended or adjusted under 35 U.S.C. 154(b) by 0 days.

(21) Appl. No.: 14/595,918

(22) Filed: Jan. 13, 2015

(65) Prior Publication Data

US 2015/0203485 A1    Jul. 23, 2015

(30) Foreign Application Priority Data

Jan. 23, 2014  (CN) .......................... 2014 1 0033146

(51) Int. Cl.
  *C07D 417/14* (2006.01)
  *H01L 51/00* (2006.01)
  *H01L 51/50* (2006.01)
(52) U.S. Cl.
  CPC .......... *C07D 417/14* (2013.01); *H01L 51/0071* (2013.01); *H01L 51/0072* (2013.01); *H01L 51/5012* (2013.01)
(58) Field of Classification Search
  CPC ..................................................... C07D 417/14
  See application file for complete search history.

(56) References Cited

U.S. PATENT DOCUMENTS

| | | | |
|---|---|---|---|
| 2012/0098002 A1 | 4/2012 | Song et al. | |
| 2012/0104376 A1 | 5/2012 | Nomura et al. | |

FOREIGN PATENT DOCUMENTS

| | | | |
|---|---|---|---|
| CN | 1601780 | A | 3/2005 |
| CN | 1658723 | A | 8/2005 |
| CN | 1979917 | A | 6/2007 |
| CN | 102050798 | A | 5/2011 |
| CN | 102516310 | A | 6/2012 |
| CN | 102596939 | A | 7/2012 |
| JP | 200415572 | A | 6/2004 |
| JP | 4196639 | B2 | 12/2008 |
| WO | 2013100465 | A1 | 7/2013 |

OTHER PUBLICATIONS

Shi et al. Spectrochimica Acta Part A 2011, 81, 730-738.*
Xu et al. Inorganica Chimica Acta 2012, 391, 50-57.*
Intellectual Property Office, Ministry of Economic Affairs, R.O.C., "Office Action", Nov. 20, 2014, Taiwan.
First Office Action issued Oct. 28, 2014 by the CN Office.
Second Office Action issued Jun. 9, 2015 by the CN Office.
Experimental and theretical study of there new benzothiazole-fused carbazole Derivatives, He-ping Shi et. al., 2011.

* cited by examiner

*Primary Examiner* — Matthew Coughlin
(74) *Attorney, Agent, or Firm* — Yunling Ren; Eaton & Van Winkle

(57) ABSTRACT

The present invention provides an organic electroluminescent material, the process for preparing same and an OLED device using same. The organic electroluminescent material has a general formula (I): wherein, each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups; each of Z is carbon atom or each of Z is nitrogen atom; R is carbazolyl, wherein, n is an integer ranging from 1 to 3 when each of Z is carbon atom, and n is an integer ranging from 1 to 2 when each of Z is nitrogen atom. The organic electroluminescent material of the invention can be used as emitting layer material in an OLED device and improve the luminescent efficiency and lifetime of the device. The luminescence spectral peak may be adjusted by changing the group on the molecular structure.

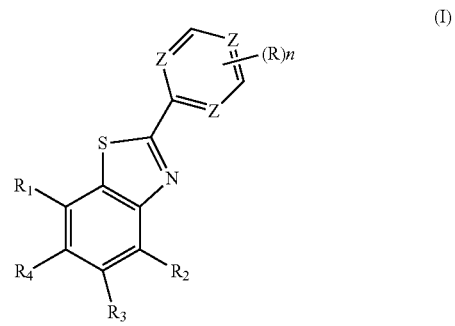

16 Claims, No Drawings

ORGANIC ELECTROLUMINESCENT MATERIAL, THE PROCESS FOR PREPARING THE SAME AND OLED DEVICE USING THE SAME

CROSS-REFERENCE TO RELATED APPLICATIONS

This application claims the benefit of the Chinese Patent Application No. 201410033146.6, filed on Jan. 23, 2014 and entitled "ORGANIC ELECTROLUMINESCENT MATERIAL, THE PROCESS FOR PREPARING THE SAME AND OLED DEVICE USING THE SAME", the content of which is incorporated by reference herein in its entirety.

TECHNICAL FIELD

The present application relates in general to a luminescent material, and in particularly to an organic electroluminescent material, the process for preparing the same and an OLED device using the same.

BACKGROUND

The organic electroluminescence phenomenon was first reported in the early 1960s. Pope and other people observed blue light when a high voltage of 400V was imposed to both sides of a single crystal of anthracene (see M. Pope, H. Kallmann and P. Magnante, J. Chem. Phys., 1963, 38, 2042). However, because the growth of the single crystal was so difficult and the driving voltage was so high, such process can almost be used in practice. Thus the development of organic electroluminescence remained stagnant.

Until 1987, by ultra-thin-film technology, C. W. Tang, hired by Kokak, a company in the United States, and other people used diamine derivatives, which had a better hole transporting effect, as the hole-transporting layer, 8-hydroxyquinoline aluminum ($Alq_3$) as emitting layer, transparent indium tin oxide (ITO) film as anode, and magnesium-silver alloy as cathode, to obtain a green light of brightness up to 1000 $Cd/m^2$ under a driving voltage of 10V. The efficiency of the device was 1.5 lm/W, and the life was above 100 hours (see C. W. Tang and S. A. Van Slyke, Appl. Phys. Lett., 1987, 51, 913). This breakthrough made the studies on organic electroluminescence being carried out rapidly and intensively in the world.

C. W. Tang first discovered that $Alq_3$ had good electroluminescent properties, 8-hydroxyquinoline and its derivatives were then used together with $Al^{3+}$, $Zn^{2+}$, $Ga^{3+}$, $Be^{2+}$, and the like to synthesize a series of complexes as electroluminescent luminescent material, and most of them emitted yellow-green light, and some emitted blue light (U.S. Pat. No. 4,720,432; U.S. Pat. No. 4,539,507; U.S. Pat. No. 5,151,629; Y. Hamada et al., Jpn. Y. Appl. Phys., Part 2, 1992, 32, L514; M. Matsumura et al., Jpn. J. Appl. Phys., 1996, 35, 5357; P. E. Burrows et al., J. Appl. Phys., 1996, 79, 7991). As disclosed in USP No. 5,432,014, Sano et al., hired by Sanyo, accompany in Japan, use Schiff base—zinc complexes as the emitting layer to prepare a blue-ray device with good performance. It is notable that 10-hydroxy-benzo-quinoline synthesized by Hamada et al., Sanyo Japan, has a better electroluminescent performance than $Alq_3$ (Y. Hamada et al., Chem. Lett., 1993, 905).

In 1996, Hamada et al. used 2-(2-hydroxy-phenyl)-benzothiazole chelated with zinc ($Zn(BTZ)_2$) as the emitting layer and the electron-transporting layer to prepare a device having a structure of indium tin oxide (ITO) (anode)/aromatic diamine derivative (TPD) (the hole-transporting layer)/Zn $(BTZ)_2$ (emitting layer)/MgIn (anode) by vacuum deposition, and emitting a green-white electroluminescence. This electroluminescence spectrum is the same as the photoluminescence spectrum; both at 486 nm and 524 nm, and having the half width of 157 nm, and the device accordingly emitted visible green-white light. The chromaticity coordinate was (0.246, 0.363), the maximum brightness may be 10190 $cd/m^2$ under a driving voltage of 8V, and the lumens efficacy was 0.89 lm/W (see Yuji Hamada, Takeshi Sano, Hiroyuki Fujii, et al, *white-light-emitting materials for organic electroluminescent devices*, Jpn. J. Appl. Phys., 1996, 35, 1339-1341).

The continuous development of organic electroluminescent material greatly promotes the progress of electroluminescent devices and makes the devices approximately into practical use. In recent years, a lot of money and effort are expended on the development of new materials, and many kinds of material of excellent properties have brought some breakthrough to the electroluminescent.

The above information disclosed in this Background section is only for enhancement of understanding of the background of the disclosure and therefore it may contain information that does not form the prior art that is already known in this country to a person of ordinary skill in the art.

SUMMARY OF THE INVENTION

The present invention aims to provide an organic electroluminescent material, which is used as emitting layer material in an OLED device and improves the luminescent efficiency and lifetime of the device. The luminescence spectral peak may be adjusted by changing the group on the molecular structure.

One object of the present invention is to provide an organic electroluminescent material having general formula (I):

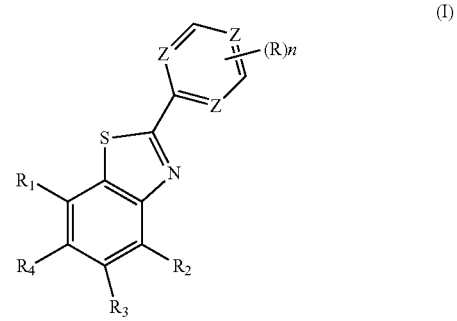

wherein:
each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups;
all of Z are carbon(C) atoms or all of Z are nitrogen(N) atoms; and
R is carbazolyl,
Wherein, n is an integer ranging from 1 to 3 when each of Z is carbon atom, and n is an integer ranging from 1 to 2 when each of Z is nitrogen atom.

According to some embodiments, each of $R_1$ and $R_2$ is independently selected from the group consisting of H, alkoxy, alkyl or ether groups; each of $R_3$ and $R_4$ is independently selected from the group consisting of H, alkyl, alkoxy and aromatic amino groups.

According to some embodiments, each of Z is carbon atom; n is 3; each of $R_1$ and $R_2$ is independently selected from the group consisting of alkoxythienyl, alkoxybithiennyl, alkoxyterphenyl, alkoxyperylenyl, alkoxystyryl, alkoxyphenylethynyl, and 7-alkoxypyrenyl; and each of $R_3$ and $R_4$ is independently selected from the group consisting of H, straight and branched $C_1$-$C_8$ alkyl, straight and branched $C_1$-$C_8$ alkoxy, diphenylamino, 4-(N,N-diphenyl)phenyl, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a red luminescent material.

According to some embodiments, each of Z is nitrogen atom; n is 2; each of $R_1$ and $R_2$ is independently selected from the group consisting of methoxy-6-pyrenyl, methoxychrysenyl, methoxyphenanthryl, methoxybenzophenanthryl, methoxybenzoanthryl, methoxyquinacridonyl, and 5-methoxynaphthacenyl-p-phenyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a green luminescent material.

According to some embodiments, each of Z is nitrogen atom; n is 1; each of $R_1$ and $R_2$ is independently selected from the group consisting of methoxyphenyl, phenoxyphenyl, methoxy-1-naphthyl, methoxy-2-naphthyl, methoxy-1-anthryl, methoxy-2-anthryl, methoxyfluorenyl, methoxyspirofluorenyl, 6-methoxypyrenyl, and 3,6-dimethoxy-N-carbazolyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a blue luminescent material.

Another object of the present invention is to provide a process for preparing the above-mentioned organic electroluminescent material, including the following steps:

a) subjecting the compound indicated by formula (II) to a boration to form the compound indicated by formula (III);

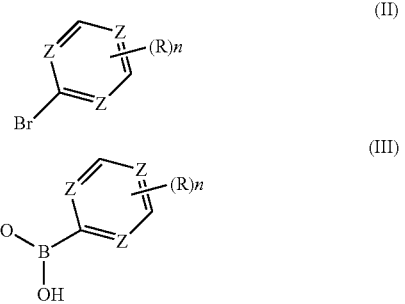

b) reacting the compound indicated by formula (III) with the compound indicated by formula (IV) in the presence of a metal catalyst, to obtain the organic electroluminescent material indicated by formula (I),

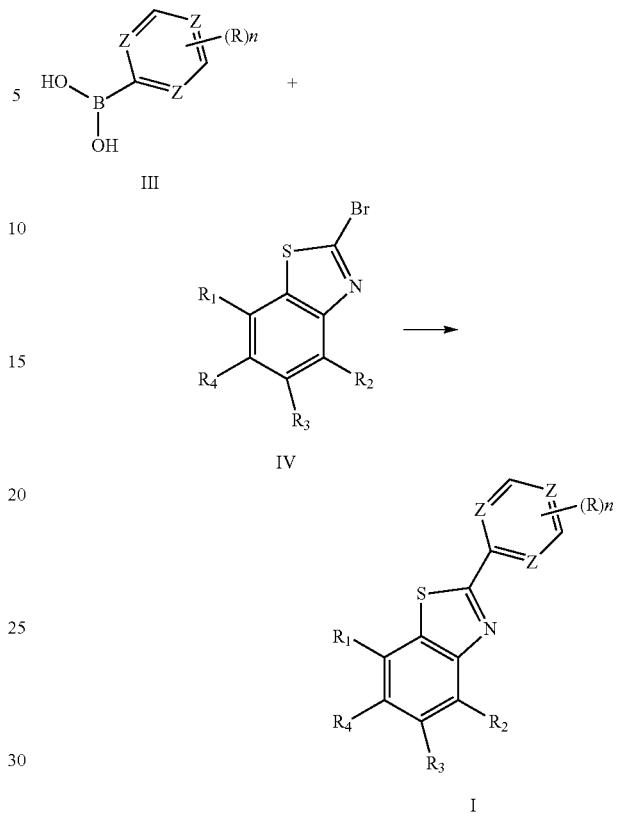

wherein:

each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups;

B is boron atom;

each of Z is carbon atom or each of Z is nitrogen atom; and

R is carbazolyl, wherein, n is an integer ranging from 1 to 3 when each of Z is carbon atom, and n is an integer ranging from 1 to 2 when each of Z is nitrogen atom.

According to some embodiments, the metal catalyst is palladium catalyst.

Still another object of the present invention is to provide an OLED device having a light emitting layer, said light emitting layer is made of the organic electroluminescent material as defined above.

The organic electroluminescent material of the present invention can be used as emitting layer material in an OLED device and improve the luminescent efficiency and lifetime of the device. The luminescence spectral peak may be adjusted by changing the group on the molecular structure.

DETAILED DESCRIPTION

The present invention will be further illustrated according to the following embodiments. It should be understood that these embodiments are only illustrative rather than limited to the present invention.

The present invention provides an organic electroluminescent material having general formula (I):

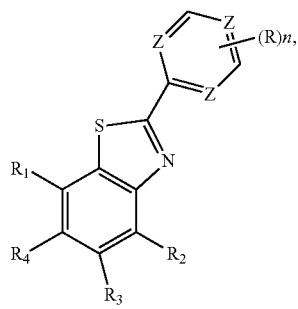

(I)

wherein:

each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups;

each of Z is carbon atom or each of Z is nitrogen atom; and

R is carbazolyl, wherein, when each of Z is carbon atom, the six-member ring is benzene, there may be 1-3 hydrogen atoms substituted by carbazolyl on the carbon, and then n is an integer ranging from 1 to 3;

When each of Z is nitrogen atom, the six-member ring is 1,3,5-triazine ring, there may be two hydrogen atoms substituted by carbazolyl on the carbon at most, and then n is an integer ranging from 1 to 2.

The above-mentioned ether groups comprise $C_1$-$C_{20}$ alkyl, substituted or unsubstituted aromatic alkyl, substituted or unsubstituted heterocyclic aromatic alkyl, and substituted or unsubstituted polycyclic aromatic alkyl, wherein the alkyl is straight and branched $C_1$-$C_8$ alkyl; the aromatic alkyl has 6 to 40 carbon atoms, such as phenyl, naphthyl, anthryl, benzoanthryl, phenanthryl, benzophenanthryl, chrysenyl, pyrenyl, perylenyl, and the like; and the heteroatoms in the heterocyclic aromatic alkyl are N, O and S, such as pyridyl, furyl, thienyl, diazinyl, triazinyl, thiazolyl, benzothiadiazolyl, benzoimidazolyl, oxadiazyl, quinolyl, indolyl, and the like.

A number of structural formulas of ether groups are as follows:

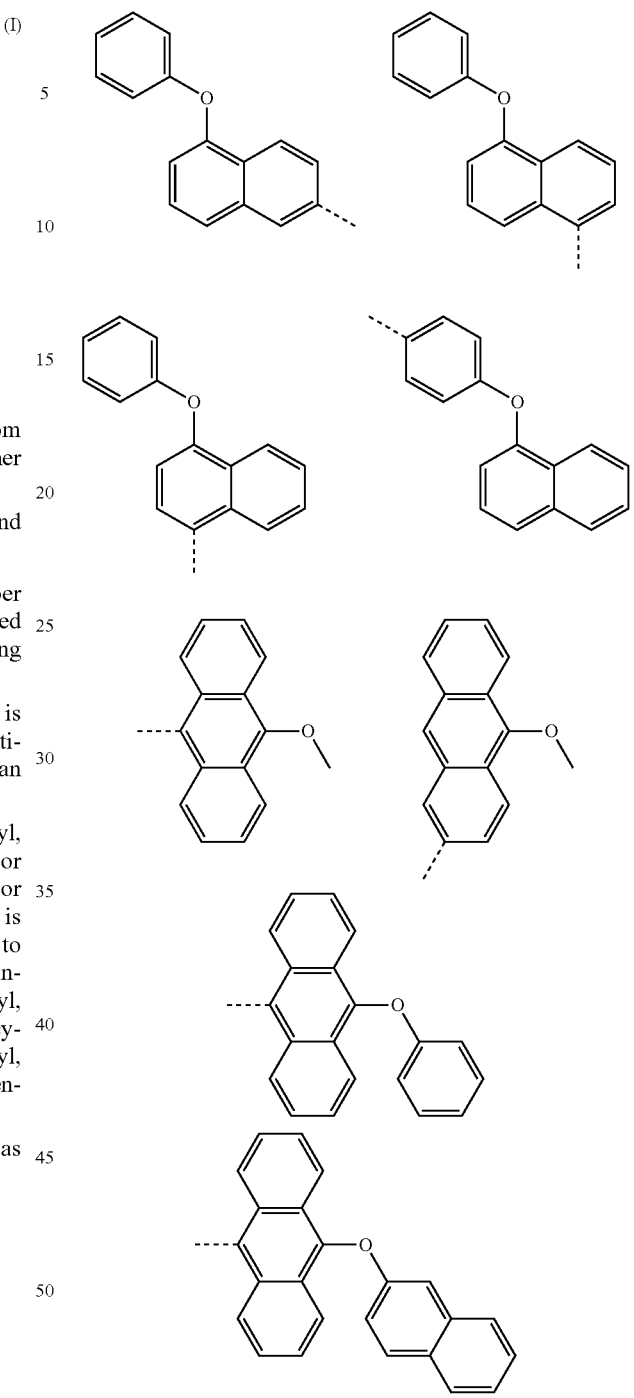

The above-mentioned aromatic amino groups comprise substituted or unsubstituted aromatic alkyl, substituted or unsubstituted heterocyclic aromatic alkyl, substituted or unsubstituted polycyclic aromatic alkyl; wherein aromatic alkyl, heterocyclic aromatic alkyl and polycyclic aromatic alkyl may specifically be phenyl, naphthyl, biphenyl, anthryl, terphenyl, phenanthryl, pyrenyl, fluorenyl, chrysenyl, benzoanthryl, benzophenanthryl, perylenyl, pyridyl, furyl, thienyl, diazinyl, triazinyl, benzothiazolyl, benzothiadiazolyl, benzoimidazolyl, oxadiazyl, quinolyl, indolyl, benzofuryl, benzothienyl, carbazolyl, and the like.

A number of structural formulas of aromatic amino groups are as follows:

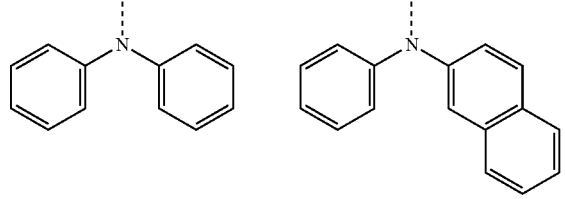
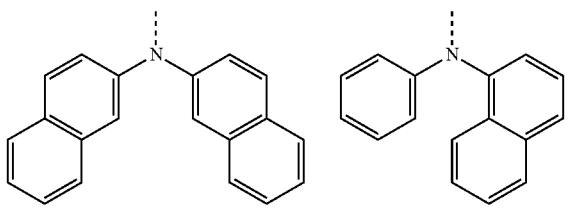
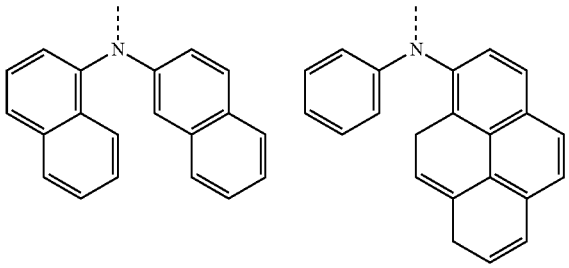
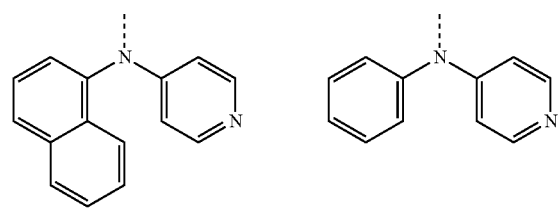
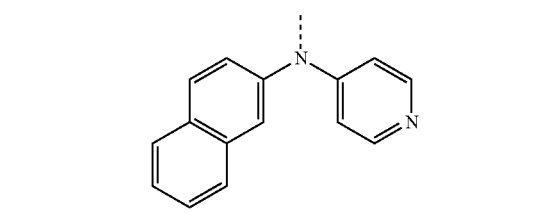
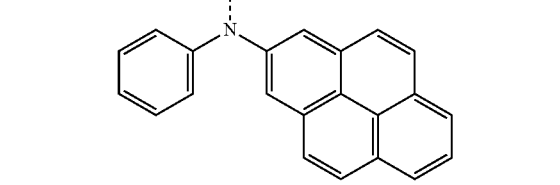
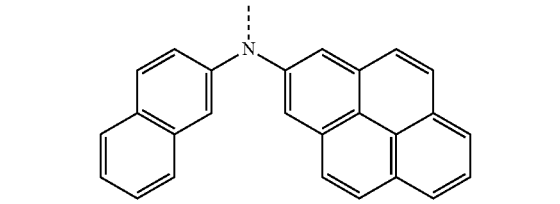

-continued

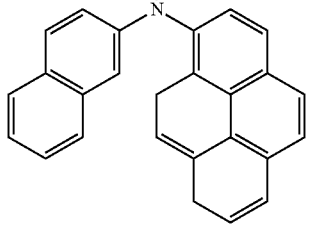
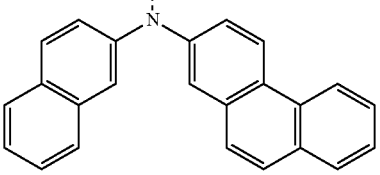

Preferably, each of $R_1$ and $R_2$ is independently selected from the group consisting of H, alkoxy, alkyl and ether groups; and each of $R_3$ and $R_4$ is independently selected from the group consisting of H, alkyl, alkoxy and aromatic amino groups.

The spectrum of the material will show red shift with the increase of the conjugation length of the molecule. According to this, the spectrum of the material may vary between blue and red by changing the degree of the conjugation of the main structure. The luminescence spectral peak of the organic electroluminescent material in the present invention depends on the selection of Z, n, $R_1$, $R_2$, $R_3$, and $R_4$.

When each of Z is carbon atom; n is 3; each of $R_1$ and $R_2$ is independently selected from the group consisting of alkoxythienyl, alkoxybithiennyl, alkoxyterphenyl, alkoxyperylenyl, alkoxystyryl, alkoxyphenylethynyl, and 7-alkoxypyrenyl; and each of $R_3$ and $R_4$ is independently selected from the group consisting of H, straight and branched $C_1$-$C_8$ alkyl, straight and branched $C_1$-$C_8$ alkoxy, diphenylamino, 4-(N,N-diphenyl)phenyl, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; the organic electroluminescent material is a red luminescent material.

When each of Z is nitrogen atom; n is 2; each of $R_1$ and $R_2$ is independently selected from the group consisting of methoxy-6-pyrenyl, methoxychrysenyl, methoxyphenanthryl, methoxybenzophenanthryl, methoxybenzoanthryl, methoxyquinacridonyl, and 5-methoxynaphthacenyl-p-phenyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; the organic electroluminescent material is a green luminescent material.

When each of Z is nitrogen atom; n is 1; each of $R_1$ and $R_2$ is independently selected from the group consisting of methoxyphenyl, phenoxyphenyl, methoxy-1-naphthyl, methoxy-2-naphthyl, methoxy-1-anthryl, methoxy-2-anthryl, methoxyfluorenyl, methoxyspirofluorenyl, 6-methoxypyrenyl, and 3,6-dimethoxy-N-carbazolyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; the organic electroluminescent material is a blue luminescent material.
The following are specific examples of the organic electroluminescent material in the present invention:
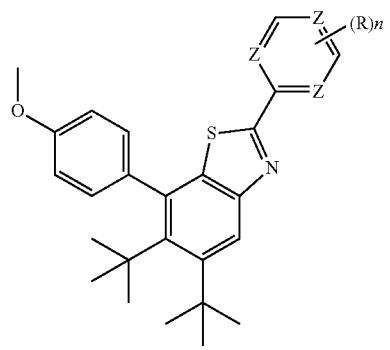
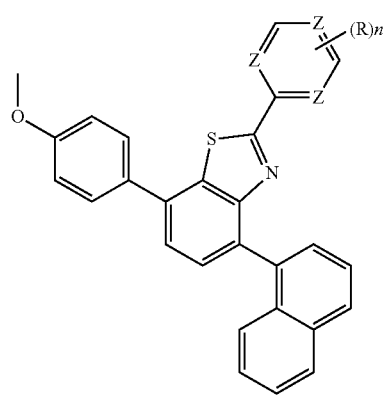
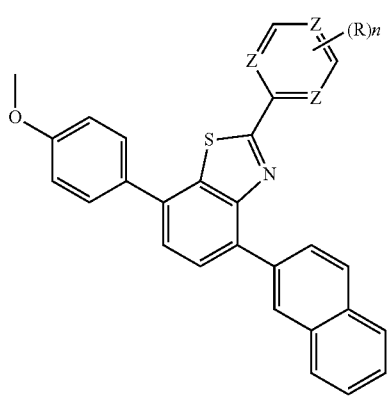
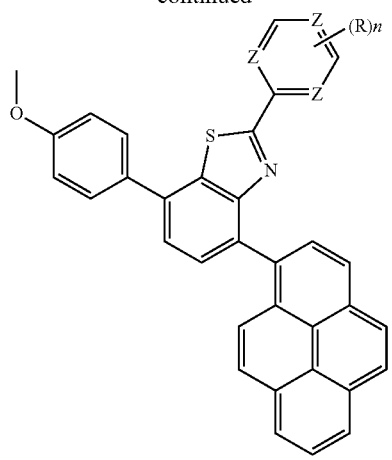
-continued
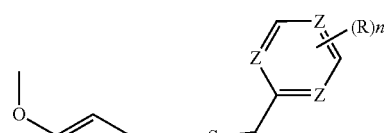
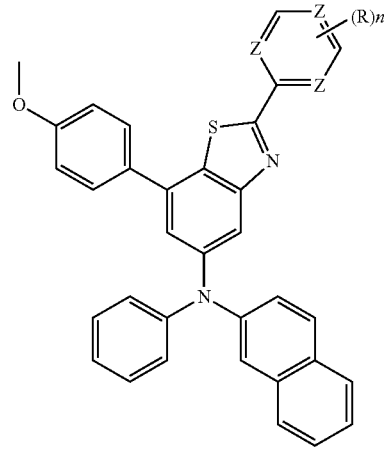
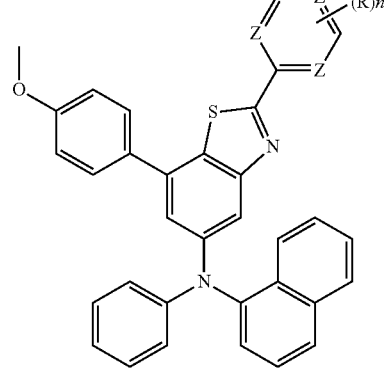

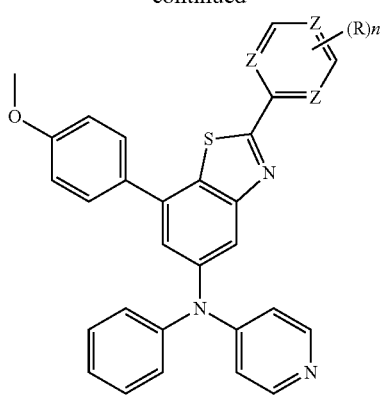

The present invention also provides a process for preparing the organic electroluminescent material, including the following steps:

a) subjecting the compound indicated by formula (II) to a boration to form the compound indicated by formula (III),

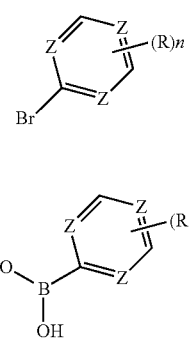

b) reacting the compound indicated by formula MD with the compound indicated by formula (IV) in the presence of a metal catalyst, to obtain the organic electroluminescent material indicated by formula (I),

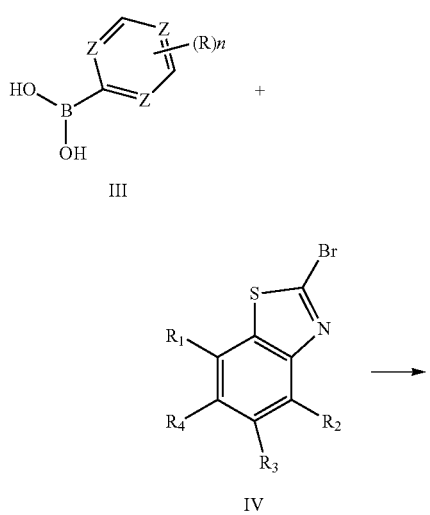

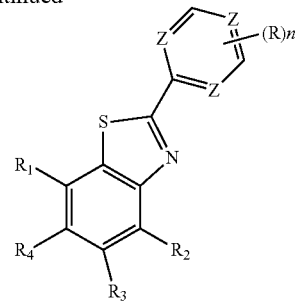

wherein:
each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups;
B is boron atom;
each of Z is carbon atom or each of Z is nitrogen atom; and
R is carbazolyl, wherein, n is an integer ranging from 1 to 3 when each of Z is carbon atom, and n is an integer ranging from 1 to 2 when each of Z is nitrogen atom.

The metal catalyst is palladium catalyst, i.e. Pd (0) catalyst.

The term "$C_1$-$C_{20}$ alkyl" as used herein refers to those alkyl groups of one to twenty carbon atoms of either a straight or branched saturated configuration. Specific examples of the alkyl include but not limited to methyl, ethyl, n-propyl and isopropyl.

The term "$C_1$-$C_{20}$ alkoxy or" as used herein refers to an alkyl group of one to twenty carbon atoms attached through an oxygen bridge. Specific examples of the alkoxy include but not limited to methoxy, ethoxy, n-propoxy, isopropoxy and the like.

The term "carbazolyl" as used herein refers to a group indicated by the following formula:

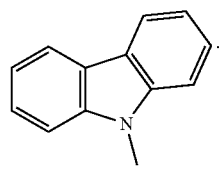

The term "boration" as used herein refers to reacting the halogenated aromatic hydrocarbon with n-BuLi (n-butyllithium) to perform a lithium-halogen exchange, then reacting it with trimethylborate and further acidified to obtain the aromatic hydrocarbon borate.

Organic light-emitting diodes generally comprise the following layers: 1. anode, 2. the hole-transporting layer, 3. emitting layer, 4. the electron-transporting layer, and 5. Cathode. Each layer has usual means appreciated by the skilled person in the art.

However, OLED may also not have all of the layers. For example, an OLED including layer (1) (anode), layer (3) (emitting layer) and layer (5) (cathode) is equally suitable. At this time, the functions of layer (2) (the hole-transporting layer) and layer (4) (the electron-transporting layer) are undertaken by the adjacent layers. Similarly, an OLED including layer (1), layer (2), layer (3) and layer (5) or including layer (1), layer (3), layer (4) and layer (5) is also suitable.

The organic electroluminescent material of the present invention may be used as emitting layer material in an OLED device.

The present invention further provide an OLED comprising at least one emitting layer of the present invention. Other layers in the OLED may be made of any known material which commonly used in such layer to the skilled person in the art.

The OLED of the present invention may be produced by any known method to the skilled person in the art, typically by vapor-depositing sequentially on a suitable substrate layers.

The terms used herein each have usual means appreciated by the skilled person in the art, except otherwise indicated.

The present invention will be described in more detail with reference to the drawings and examples. It should be understood that the examples are provided for illustrating rather than limiting the present application.

EXAMPLE

Unless specifically stated otherwise, the crude material, the solvent and the catalyst used in the present invention can be obtained from Sigma-Aldrich.

Example 1

Under an Ar atmosphere, 3,5-dicarbazolylbromobenzene (4.87 g, 0.01 mol) and 100 mL THF (tetrahydrofuran) were added into a 250 mL single-necked flask, then 9.4 mL n-BuLi (n-butyllithium) (1.6 M n-hexane solution) was added, stirred and reacted at −78° C. for 1.5 h. After this, trimethyl borate was added and reacted for 12 h, and then 20 mL hydrochloric acid solution was added, acidified for 0.5 h. After the reaction was completed, we carried out liquid separation, drying, and concentrating under reduced pressure, and obtained 3,5-dicarbazolylphenylboronic acid by column chromatography. The reaction process is as follows:

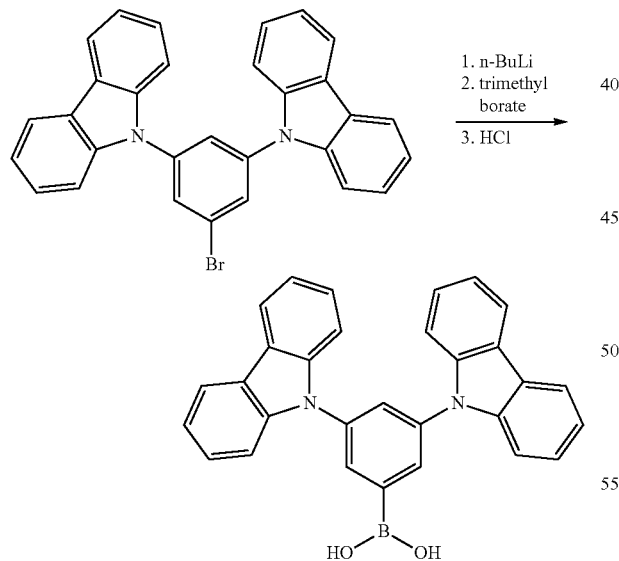

Under an Ar atmosphere, 0.1 mol 3,5-dicarbazolylphenylboronic acid and 0.1 mol 2-bromo-5-methylbenzothiazole were dissolved into a solution mixed by 250 ml toluene and 50 ml 2M $K_2CO_3$ aqueous solution in a 500 mL round bottom flask. Pd (0) catalyst was added and the mixed solution was stirred and heated at 90° C. reflux for 24 hours. Then we cooled it to room temperature, removed the organic solvent by vacuum-concentration using a rotary evaporator and obtained a crude product. The resulting crude product was purified by recrystallization using toluene/n-hexane as solvent, and dried in vacuum at 50° C. We obtained the final product as shown in Formula 1-1. The reaction process is as follows:

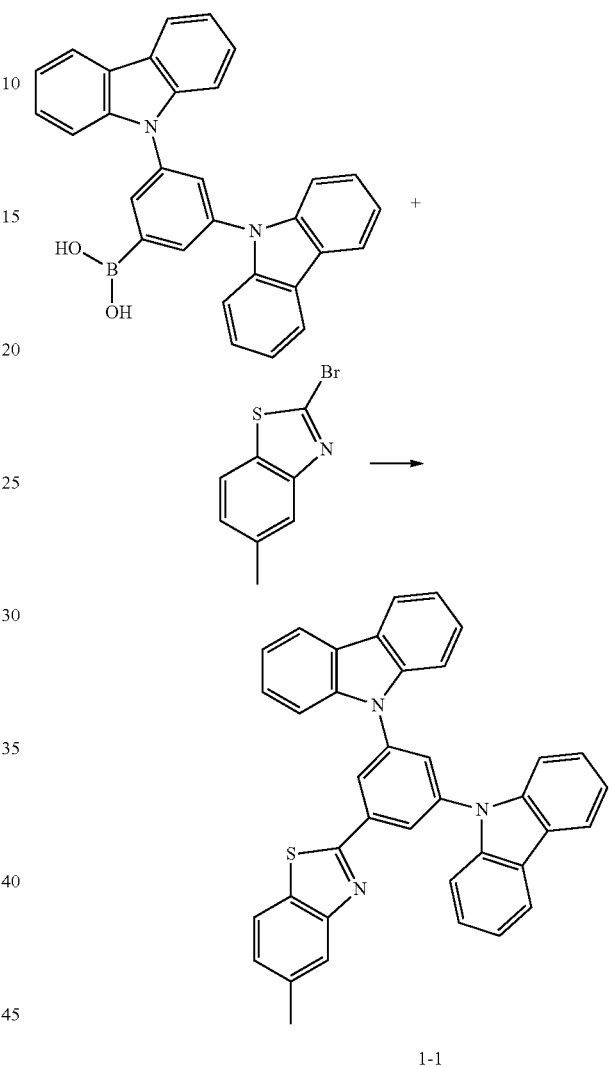

1-1

We subject the compound obtained in Example 1 to (a) mass spectrometry (MS), (b) Nuclear magnetic resonance analysis (NMR), and (c) measuring the fluorescence spectra peaks, and the result is as follows:

(a) MS[TOF] m/z=555;

(b) $^1$H-NMR (400 MHz, CDCl$_3$) δ (ppm): 8.56-8.51 (d, 2H), 8.32-8.11 (m, 4H), 7.89-7.68 (m, 4H), 7.58-7.56 (d, 2H), 7.43-7.14 (m, 10H), 2.13 (s, 3H).

The analytic results of (a) and (b) authenticate that the final product as shown in Formula 1-1 is obtained by the synthesis method in Example 1, and the result of (c) is shown in Table 1.

Example 2

The synthesis of 3,5-dicarbazolylphenylboronic acid is the same as Example 1.

Under an Ar atmosphere, 0.1 mol 3,5-dicarbazolylphenylboronic acid and 0.1 mol 2-bromo-5-methyl-7-(p-methoxyphenyl)benzothiazole were dissolved into a solution mixed by 250 ml toluene and 50 ml 2M K₂CO₃ aqueous solution in a 500 mL round bottom flask. Pd (0) catalyst was added and the mixed solution was stirred and heated at 90° C. reflux for 24 hours. Then we cooled it to room temperature, removed the organic solvent by vacuum-concentration using a rotary evaporator and obtained a crude product. The resulting crude product was purified by recrystallization using toluene/n-hexane as solvent, and dried in vacuum at 50° C. We obtained the final product as shown in Formula 2-1. The reaction process is as follows:

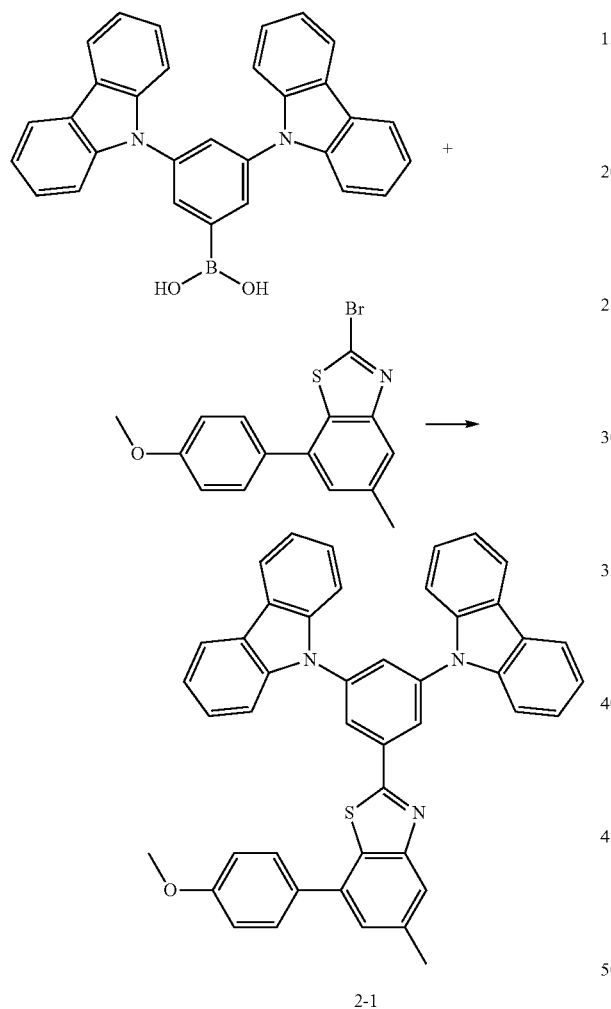

2-1

We subject the compound obtained in Example 2 to (a) mass spectrometry (MS), (b) Nuclear magnetic resonance analysis (NMR), and (c) measuring the fluorescence spectra peaks, and the result is as follows:

(a) MS[TOF]m/z=661.

(b) ¹H-NMR (400 MHz, CDCl₃) δ (ppm): 8.55-8.50 (d, 2H), 8.12-8.08 (m, 4H), 7.94-7.92 (d, 2H), 7.85 (s, 1H), 7.68-7.55 (m, 7H), 7.49-7.31 (m, 7H), 7.06 (d, 2H), 4.75 (s, 3H), 2.43 (s, 3H).

The analytic results of (a) and (b) authenticate that the final product as shown in Formula 2-1 is obtained by the synthesis method in Example 2, and the result of (c) is shown in Table 1.

TABLE 1

Structure and luminescence spectral peak the of the compound obtained in Example 1 and Example 2

| | R₁ | R₂ | R₃ | R₄ | Z | n | Luminescence spectral peak |
|---|---|---|---|---|---|---|---|
| Example 1 | H | H | CH₃ | H | C | 2 | 500-520 nm |
| Example 2 | p-methoxyphenyl | H | CH₃ | H | C | 2 | 500-520 nm |

Practical Example

Manufacture of the OLED

Practical Example 1

Luminescent Device [ITO/NPB/1-1/TPBI/LiF/Al]

Manufactured the OLED device by using the organic electroluminescent material 1-1 in Example 1, Steps were as follows:

Deposited a NPB hole-transporting layer on a glass substrate coated by ITO (indium tin oxide) (positive electrode), the thickness of which was 150 Å; deposited an emitting layer using the organic electroluminescent material 1-1, the thickness of which was 50 Å; deposited a hole blocking layer TPBI having a thickness of 750 Å; deposited a LiF layer having a thickness of 5 Å; finally deposited an Al layer (negative electrode) having a thickness of 2000 Å, and obtained the OLED device.

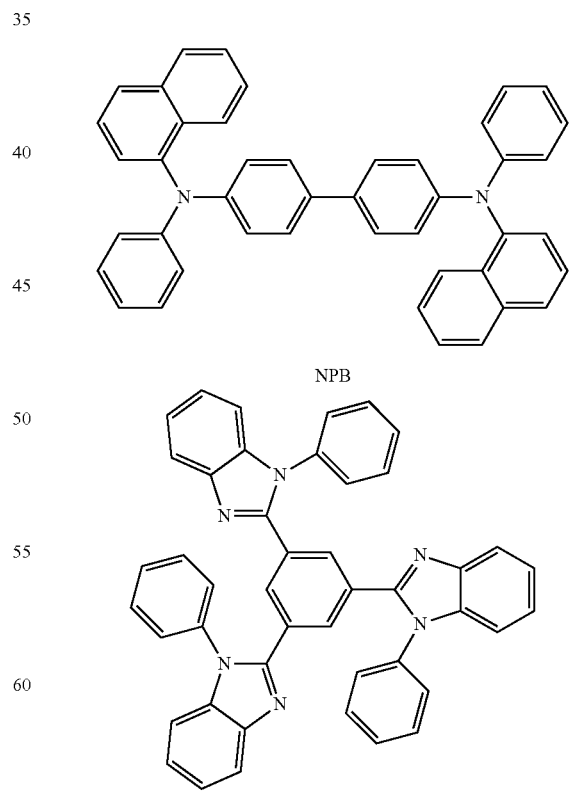

NPB

TPBI

The performance of the obtained OLED device was tested, and the results were shown in Table 2.

Practical Example 2

Luminescent Device [ITO/NPB/2-1/TPBI/LiF/Al]

Manufactured the OLED device using the same method as in Practical Example 1, except that the emitting layer was made by using the organic electroluminescent material 2-1 in Example 2. The performance of the obtained OLED device was tested, and the results were shown in Table 2.

TABLE 2

The performance of obtained OLED devices in Practical Example 1 and Practical Example 2 @1000 nits

| | Maximum efficiency | Luminescence lifetime (T50) | Luminescence spectral peak | Chromaticity coordinate |
|---|---|---|---|---|
| Practical Example 1 | 6-8 cd/A | 7000-10000 h | 512 nm | (0.3, 0.62) |
| Practical Example 2 | 6-10 cd/A | 7000-10000 h | 518 nm | (0.3, 0.62) |

In summary, the organic electroluminescent material of the present invention can be used as emitting layer material in an OLED device and improve the luminescent efficiency and lifetime of the device. The luminescence spectral peak may be adjusted by changing the group on the molecular structure.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An organic electroluminescent material having general formula (I):

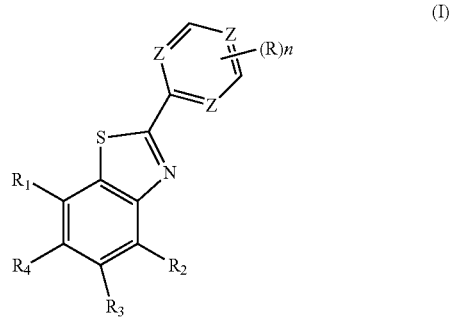

wherein:
each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups;
each of Z is carbon atom or each of Z is nitrogen atom; and R is carbazolyl,
wherein, n is an integer ranging from 2 to 3 when each of Z is carbon atom, and n is an integer ranging from 1 to 2 when each of Z is nitrogen atom.

2. The organic electroluminescent material according to claim 1, wherein each of $R_1$ and $R_2$ is independently selected from the group consisting of H, $C_1$-$C_{20}$ alkoxy, $C_1$-$C_{20}$ alkyl and ether groups, and each of $R_3$ and $R_4$ is independently selected from the group consisting of H, $C_1$-$C_{20}$ alkyl, $C_1$-$C_{20}$ alkoxy and aromatic amino groups.

3. The organic electroluminescent material according to claim 1, wherein each of Z is carbon atom; n is 3; each of $R_1$ and $R_2$ is independently selected from the group consisting of alkoxythienyl, alkoxybithiennyl, alkoxyterphenyl, alkoxyperylenyl, alkoxystyryl, alkoxyphenylethynyl, and 7-alkoxypyrenyl; and each of $R_3$ and $R_4$ is independently selected from the group consisting of H, straight and branched $C_1$-$C_8$ alkyl, straight and branched $C_1$-$C_8$ alkoxy, diphenylamino, 4-(N,N-diphenyl)phenyl, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a red luminescent material.

4. The organic electroluminescent material according to claim 1, wherein each of Z is nitrogen atom; n is 2; each of $R_1$ and $R_2$ is independently selected from the group consisting of methoxy-6-pyrenyl, methoxychrysenyl, methoxyphenanthryl, methoxybenzophenanthryl, methoxybenzoanthryl, methoxyquinacridonyl, and 5-methoxynaphthacenyl-p-phenyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a green luminescent material.

5. The organic electroluminescent material according to claim 1, wherein each of Z is nitrogen atom; n is 1; each of $R_1$ and $R_2$ is independently selected from the group consisting of methoxyphenyl, phenoxyphenyl, methoxy-1-naphthyl, methoxy-2-naphthyl, methoxy-1-anthryl, methoxy-2-anthryl, methoxyfluorenyl, methoxyspirobifluorenyl, 6-methoxypyrenyl, and 3,6-dimethoxy-N-carbazolyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a blue luminescent material.

6. A process for preparing the organic electroluminescent material as defined in claim 1, including the following steps:
a) subjecting the compound indicated by formula (II) to a boration to form The compound indicated by formula (III),

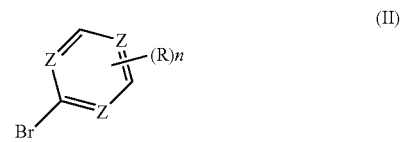

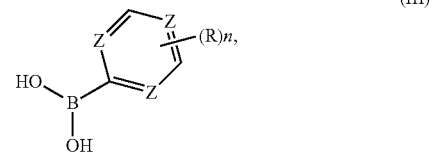

b) reacting the compound indicated by formula (III) with the compound indicated by formula (IV) in the presence of a metal catalyst, to obtain the organic electroluminescent material indicated by formula (I),

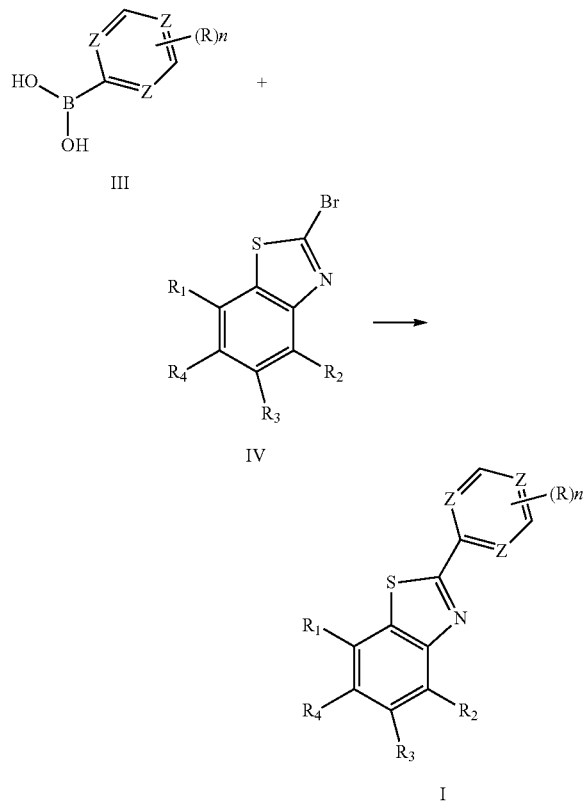

wherein:
each of $R_1$, $R_2$, $R_3$ and $R_4$ is independently selected from the group consisting of H, $C_1$-$C_{20}$ alkyl, $C_1$-$C_{20}$ alkoxy, ether groups and aromatic amino groups;
B is boron atom;
each of Z is carbon atom or each of Z is nitrogen atom; and
R is carbazolyl, wherein, n is an integer ranging from 2 to 3 when each of Z is carbon atom, and n is an integer ranging from 1 to 2 when each of Z is nitrogen atom.

7. The process according to claim 6, wherein the metal catalyst is palladium catalyst.

8. The process according to claim 6, wherein each of $R_1$ and $R_2$ is independently selected from the group consisting of H, $C_1$-$C_{20}$ alkoxy, $C_1$-$C_{20}$ alkyl and ether groups, and each of $R_3$ and $R_4$ is independently selected from the group consisting of H, $C_1$-$C_{20}$ alkyl, alkoxy and aromatic amino groups.

9. The process according to claim 6, wherein each of Z is carbon atom; n is 3; each of $R_1$ and $R_2$ is independently selected from the group consisting of alkoxythienyl, alkoxybithiennyl, alkoxyterphenyl, alkoxyperylenyl, alkoxystyryl, alkoxyphenylethynyl, and 7-alkoxypyrenyl; and each of $R_3$ and $R_4$ is independently selected from the group consisting of H, straight and branched $C_1$-$C_8$ alkyl, straight and branched $C_1$-$C_8$ alkoxy, diphenylamino, 4-(N,N-diphenyl)phenyl, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a red luminescent material.

10. The process according to claim 6, wherein each of Z is nitrogen atom; n is 2; each of $R_1$ and $R_2$ is independently selected from the group consisting of methoxy-6-pyrenyl, methoxychrysenyl, methoxyphenanthryl, methoxybenzophenanthryl, methoxybenzoanthryl, methoxyquinacridonyl, and 5-methoxynaphthacenyl-p-phenyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a green luminescent material.

11. The process according to claim 6, wherein each of Z is nitrogen atom; n is 1; each of $R_1$ and $R_2$ is independently selected from the group consisting of methoxyphenyl, phenoxyphenyl, methoxy-1-naphthyl, methoxy-2-naphthyl, methoxy-1-anthryl, methoxy-2-anthryl, methoxyfluorenyl, methoxyspirobifluorenyl, 6-methoxypyrenyl, and 3,6-dimethoxy-N-carbazolyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a blue luminescent material.

12. An OLED device having a light emitting layer, said light emitting layer is made of an organic electroluminescent material as defined in claim 1.

13. The OLED device according to claim 12, wherein each of $R_1$ and $R_2$ is independently selected from the group consisting of H, $C_1$-$C_{20}$ alkoxy, $C_1$-$C_{20}$ alkyl and ether groups, and each of $R_3$ and $R_4$ is independently selected from the group consisting of H, $C_1$-$C_{20}$ alkyl, $C_1$-$C_{20}$ alkoxy and aromatic amino groups.

14. The OLED device according to claim 12, wherein each of Z is carbon atom; n is 3; each of $R_1$ and $R_2$ is independently selected from the group consisting of alkoxythienyl, alkoxybithiennyl, alkoxyterphenyl, alkoxyperylenyl, alkoxystyryl, alkoxyphenylethynyl, and 7-alkoxypyrenyl; and each of $R_3$ and $R_4$ is independently selected from the group consisting of H, straight and branched $C_1$-$C_8$ alkyl, straight and branched $C_1$-$C_8$ alkoxy, diphenylamino, 4-(N,N-diphenyl)phenyl, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a red luminescent material.

15. The OLED device according to claim 12, wherein each of Z is nitrogen atom; n is 2; each of $R_1$ and $R_2$ is independently selected from the group consisting of methoxy-6-pyrenyl, methoxychrysenyl, methoxyphenanthryl, methoxybenzophenanthryl, methoxybenzoanthryl, methoxyquinacridonyl, and 5-methoxynaphthacenyl-p-phenyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a green luminescent material.

16. The OLED device according to claim 12, wherein each of Z is nitrogen atom; n is 1; each of $R_1$ and $R_2$ is independently selected from the group consisting of methoxyphenyl, phenoxyphenyl, methoxy-1-naphthyl, methoxy-2-naphthyl, methoxy-1-anthryl, methoxy-2-anthryl, methoxyfluorenyl, methoxyspirobifluorenyl, 6-methoxypyrenyl, and 3,6-dimethoxy-N-carbazolyl; and each of $R_3$ and $R_4$ is independently selected from the group consisting of H, straight and branched $C_1$-$C_8$ alkyl, straight and branched $C_1$-$C_8$ alkoxy, diphenylamino, N-phenylnaphthyl-2-amino, dinaphthylamino, N-phenylpyridin-2-amino, N-phenylpyrenyl-1-amino, N-phenylpyrenyl-2-amino, N-phenylbiphenyl-4-amino, N-phenylphenanthryl-2-amino, and N-phenylanthryl-2-amino; and the organic electroluminescent material is a blue luminescent material.

\* \* \* \* \*